US009918894B2

(12) United States Patent
Lam et al.

(10) Patent No.: US 9,918,894 B2
(45) Date of Patent: Mar. 20, 2018

(54) METHODS AND VIEWING SYSTEMS FOR INHIBITING OCULAR REFRACTIVE DISORDERS FROM PROGRESSING

(71) Applicants: Siu Yin Lam, Kowloon (HK); Yan Yin Tse, Kowloon (HK); Chi Ho To, Kowloon (HK)

(72) Inventors: Siu Yin Lam, Kowloon (HK); Yan Yin Tse, Kowloon (HK); Chi Ho To, Kowloon (HK)

( * ) Notice: Subject to any disclaimer, the term of this patent is extended or adjusted under 35 U.S.C. 154(b) by 7 days.

(21) Appl. No.: 15/009,224

(22) Filed: Jan. 28, 2016

(65) Prior Publication Data

US 2016/0143801 A1 May 26, 2016

Related U.S. Application Data

(62) Division of application No. 13/568,016, filed on Aug. 6, 2012, now abandoned.

(51) Int. Cl.
*A61B 3/00* (2006.01)
*A61H 5/00* (2006.01)

(52) U.S. Cl.
CPC .................................... *A61H 5/00* (2013.01)

(58) Field of Classification Search
CPC ........ A61B 3/1015; A61B 3/103; G02C 7/04; G02C 7/02; A61F 2009/00872
USPC ...................................... 351/159.73, 159.78
See application file for complete search history.

(56) References Cited

U.S. PATENT DOCUMENTS 2,388,858 A * 11/1945 MacNeille ............... A61B 3/08 351/159.58
4,408,846 A * 10/1983 Balliet .................. A61B 3/032 351/203
4,533,221 A * 8/1985 Trachtman .............. A61B 3/09 351/203

(Continued)

OTHER PUBLICATIONS

Diether, S.; Wildsoet, C. F. , "Stimulus requirements for the decoding of myopic and hyperopic defocus under single and competing defocus conditions in the chicken." Invest Ophthalmol Vis Sci 46(7): 2242-2252 (2005).

(Continued)

*Primary Examiner* — James Greece
(74) *Attorney, Agent, or Firm* — George A. Leone; Citadel Patent Law

(57) ABSTRACT

A method for retarding or reversing progression of myopia of a viewer includes providing an object in front of the viewer; providing a transparent layer between the viewer and the object; and providing a primary image on the transparent layer, the transparent layer allows the viewer to see the object as a secondary image simultaneously with the primary image, wherein the secondary image is focused in front of the central region of the retina. A method for reducing hyperopia of a viewer includes providing an object in front of the viewer to provide a primary image; providing a transparent layer between the viewer and the object; providing a secondary image on the transparent layer, the transparent layer allows the viewer to see the primary image simultaneously with the secondary image, wherein the secondary image is focused behind the central region of the retina. Other systems are also described herein.

5 Claims, 12 Drawing Sheets

(56) References Cited

U.S. PATENT DOCUMENTS

| | | | | | |
|---|---|---|---|---|---|
| 4,660,945 | A * | 4/1987 | Trachtman | A61B 3/09 351/203 |
| 4,778,268 | A * | 10/1988 | Randle | A61H 5/00 351/203 |
| 5,088,810 | A * | 2/1992 | Galanter | A61H 5/00 351/203 |
| 5,757,458 | A * | 5/1998 | Miller et al. | 351/159.02 |
| 6,033,073 | A * | 3/2000 | Potapova | A61B 5/04842 351/211 |
| 6,155,682 | A * | 12/2000 | Steinberg | G02C 7/14 351/205 |
| 2006/0082729 | A1* | 4/2006 | To et al. | 351/246 |
| 2010/0103075 | A1* | 4/2010 | Kalaboukis | A63F 13/02 345/8 |
| 2012/0062836 | A1* | 3/2012 | Tse et al. | 351/161 |

OTHER PUBLICATIONS

Tse, D. Y.; To, C. H., "Graded competing regional myopic and hyperopic defocus produce summated emmetropization set points in chick." Investigative ophthalmology & visual science 52(11): 8056-8062. (2011).

Tse Y. et al., "Spatial frequency and myopic defocus detection in chick eye in a closed visual environment." ARVO, For Lauderdale.

U.S. Appl. No. 13/568,016, Notice of Restriction/Election of Claims, dated Jun. 10, 2015.

U.S. Appl. No. 13/568,016, Response to Restriction/Election of Claims, dated Jul. 31, 2015.

U.S. Appl. No. 13/568,016, Non-Final Office Action, dated Aug. 28, 2015.

U.S. Appl. No. 13/568,016, Notice of Abandonment, dated Mar. 11, 2016.

* cited by examiner

METHODS AND VIEWING SYSTEMS FOR INHIBITING OCULAR REFRACTIVE DISORDERS FROM PROGRESSING

RELATED APPLICATION

This application claims priority from and is a divisional of co-pending U.S. application Ser. No. 13/568,016 of Lam, et al., filed Aug. 6, 2012, entitled "Methods and Viewing Systems for Inhibiting Ocular Refractive Disorders from Progressing." U.S. application Ser. No. 13/568,016 of Lam, et al., is hereby incorporated by reference.

TECHNICAL FIELD

The present invention relates to methods and systems for inhibiting the development or progression of refractive disorders of an eye, with the emphasis on myopia and/or hyperopia.

BACKGROUND OF THE INVENTION

Shortsightedness or myopia and farsightedness or hyperopia are common refractive disorders of human eyes. Objects beyond a distance from a myopic person are focused in front of the retina, and objects beyond a distance from a hyperopic person are focused behind the retina, and consequently the objects are perceived as blurry images.

Myopia develops when the eye grows excessively larger than the focal length of the eye. Myopia usually progresses in human eyes over time and is typically managed by regularly renewed prescriptions of optical lenses such as corrective spectacles and contact lenses. Those lenses provide clear vision but do not retard progression of myopia. Undesirable sight-threatening eye diseases are also associated with high levels of myopia.

Hyperopia is usually congenital, when the size of the eye has not grown enough and is shorter than the focal length of the eye. Without proper management, hyperopia may associate with blurred vision, amblyopia, asthenopia, accommodative dysfunction and strabismus. Hyperopia is typically managed by prescriptions of corrective optical lenses which temporarily provide clear vision but do not heal or eliminate the disorder permanently.

Therefore, there is a need for new technology to reduce the economic and social burden produced by refractive disorders such as common myopia and hyperopia by providing clear vision and a retardation function at the same time. Recent scientific publications have stated that the dimensional growth of developing eyes is modulated by optical defocus, which results when images are projected away from the retina. Refractive development of the eye is influenced by the equilibrium between defocus of opposite directions. In particular, it has been documented that artificially induced "myopic defocus" (an image projected in front of the retina) may retard myopia from progressing further. In this context, the position of "in front of the retina" refers to any position between the retina and the lens of an eye but not on the retina.

WO 2006/034652, to To, 6 Apr. 2006 suggests the use of concentric multi-zone bifocal lenses in which myopic defocus is induced both axially and peripherally for visual objects of all viewing distances. Those methods have been shown to be effective in both animal study and human clinical trial for retarding myopia progression. However, those methods comprise the prescription and the use of specialty lenses which may not be suitable for all people.

Similar disadvantages apply for the other contact lens designs such as U.S. Pat. No. 7,766,478 B2, to Phillips, published Aug. 3, 2010; U.S. Pat. No. 7,832,859, to Phillips, published 16 Nov. 2010; U.S. Pat. No. 7,503,655 to Smith, et al., published 17 Mar. 2009; and U.S. Pat. No. 7,025,460 to Smith, et al., published 11 Apr. 2006.

U.S. Pat. No. 7,503,655 and U.S. Pat. No. 7,025,460, both above, suggest methods to counteract myopia by manipulating peripheral optics, inducing relative peripheral myopic defocus without inducing myopic defocus on the central retina. Since it is known that the protective effect of defocus is directly correlated with the area of retinal area exposed to it, their design may not achieve maximum effectiveness as defocus is not induced on the central retina.

Accordingly the need remains for improved methods, apparatuses, and/or systems for inhibiting and potentially reducing or even curing refractive disorders of a viewer. Therefore it is an objective of the current invention which make use of novel viewing systems instead of specialty lenses, to overcome or ameliorate at least one of the disadvantages of the prior art, or to provide a useful alternative.

SUMMARY OF THE INVENTION

According to the present invention, there is provided a method for retarding or reversing progression of myopia of a viewer. The viewer has a retina with a central region. The method comprising the step of providing an object in front of the viewer; providing a transparent layer between the viewer and the object and providing a primary image on the transparent layer. The transparent layer allows the viewer to see the object as a secondary image simultaneously with the primary image, wherein the secondary image is focused in front of the central region of the retina.

In another preferred embodiment, there is provided a method for reducing hyperopia of a viewer. The viewer has a retina with a central region. The method comprising the step of providing an object in front of the viewer to provide a primary image; providing a transparent layer between the viewer and the object and providing a secondary image on the transparent layer. The transparent layer allows the viewer to see the primary image simultaneously with the secondary image, wherein the secondary image is focused behind the central region of the retina.

In another preferred embodiment, there is provided an optical system comprising a transparent layer, the transparent layer adapted to provide a primary image and a secondary image. The secondary image is provided by an object behind the transparent layer being viewed through the transparent layer by a viewer having a retina.

In another preferred embodiment, there is provided an optical system comprising at least one layer. The at least one layer adapted to display a primary image and a secondary image generated by a computer program. The primary image and the secondary image are simultaneously viewable by a viewer having a retina with a central region, wherein the primary image is focused on the retina, and the secondary image is focused in front of or behind the central region.

In another preferred embodiment, there is provided a method for retarding or reversing progression of myopia a viewer. The viewer has a retina with a central region. The method comprising the steps of providing a layer having a reflective surface, said reflective surface facing the viewer; providing an object facing the reflective surface and providing a primary image on the layer, said primary image being viewable by the viewer.

The reflective surface allows reflection of the object to be viewed by the viewer as a secondary image, with the secondary image being focused in front of the central region of the retina.

In another preferred embodiment, there is provided an optical system comprising a layer having a reflective surface. The layer adapted to provide a primary image and a secondary image. The secondary image is provided by a reflection of an object facing the reflective surface, the primary and the secondary images are viewable by a viewer having a retina.

BRIEF DESCRIPTION OF THE DRAWINGS

Examples of the invention will now be described with reference to the accompanying drawings, in which.

Figure 1A:
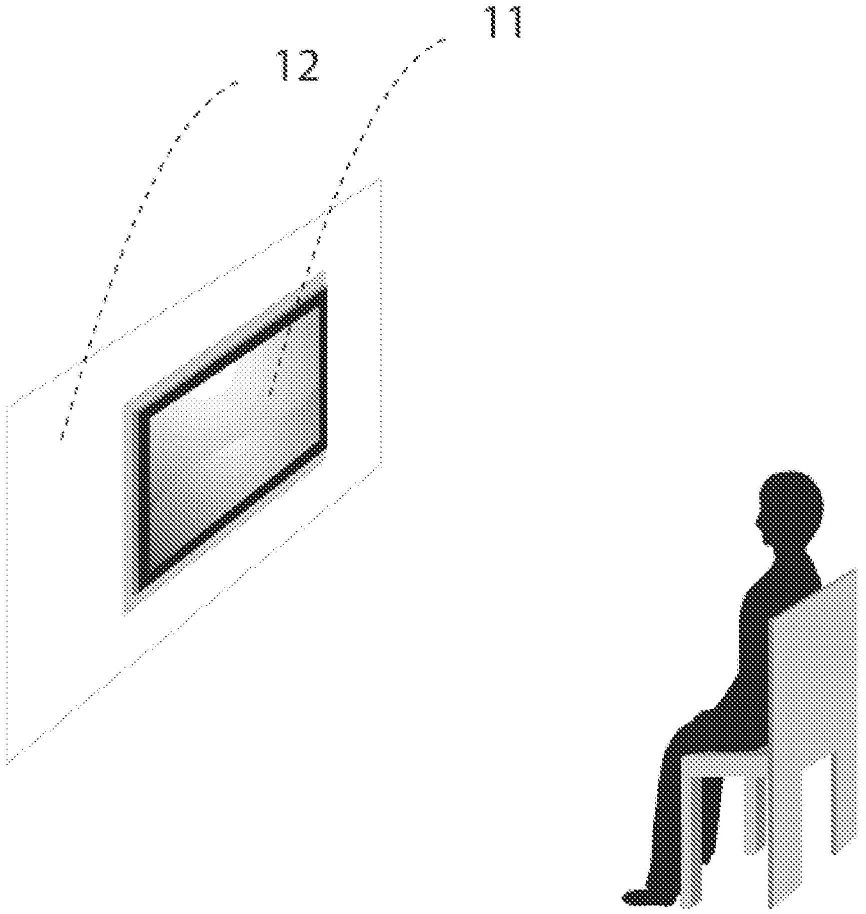
FIG. 1A is a diagram showing the way a conventional visual display unit is used.

The figures herein are not necessarily drawn to scale.

DETAILED DESCRIPTION

The invention relates to a method for preventing, retarding, and/or reversing progression of refractive disorders of any eye, including myopia or hyperopia of a human eye. In an embodiment herein the invention relates to a method for preventing progression of a reflective disorder. In an embodiment herein, the invention relates to a method for retarding progression of a reflective disorder. In an embodiment herein, the invention relates to a method of reversing a refractive disorder.

For preventing or retarding progression of myopia, a method including producing a focused image on the retina of the human eye for viewing and simultaneously creating a defocused image in front of the retina for generating myopic defocus is described here below. Particularly, the method includes generating myopic defocus on at least the central region of the retina for achieving a treatment effect. For preventing or reducing progression of hyperopia, the method includes producing a focused image on the retina of the human eye for viewing and simultaneously creating a defocused image behind the retina for generating hyperopic defocus.

Traditional viewing systems display visual information on a single plane. When being viewed, the primary visual object such as text and graphic is focused on the retina, inducing no defocus stimuli (or small amount of myopia-inducing hyperopic defocus if the users exhibit the habit of accommodative lag). The current invention makes use of a transparent or a reflective optical layer allowing secondary object behind or in front of the layer, respectively, to be seen simultaneously when the primary visual object is viewed. The secondary object, being positioned on different dioptric planes, is projected either in front of the retina to produce myopia-retarding myopic defocus stimuli, or behind the retina to produce hyperopia-reducing hyperopic defocus stimuli.

Transparency is commonly defined as the ability of a material to allow light to pass though itself without scattering. In this context, the transparency of the layer is a term in optical physics that describes the proportion of light transmitted through a layer which is quantifiable, adjustable and measurable between 0% to 100%. Accordingly, the meaning of the term “transparent” is not limited to the literal meaning of being totally transparent but also “partially transparent” or “being transparent or partially transparent regionally”. Within the context of this disclosure, the term “transparent” with respect to a layer of material means that between about 100% and about 70%, or between about 100% and 80%, or between about 100% and about 85% of the visible light is transmitted through the layer.

Reflectance is commonly defined as the percentage of light being reflected by a surface. In this context, the meaning of the term “reflective” refers to being “light reflective”. The term is not limited to the literal meaning of being totally reflective but also “partially reflective” or “being reflective or partially reflective regionally”.

The transparent layer or the reflective layer as referred to in the embodiments of the present invention can be a physical screen (for the transparent or reflective layer) or a virtual imaging plane (for the transparent layer in view of the available technology) produced by various technologies including but not limited to a liquid crystal display, an organic light emitting diode, a screen projection system, a holographic display, a partial mirror, a multiscopic visualization, a volume multiplexing visualization, or a combination thereof.

The system as referred to in the embodiments of the present invention can be a permanent home, office or gymnasium visual displaying environment including components such as a desktop personal computer, a television, a theater system or a combination thereof. The system may also be a compact portable unit or an electronic device such as an electronic book reader, a tablet computer, a portable display, a portable computer, other media or a gaming system.

A number of non-limiting examples for retarding or reversing the progression of refractive disorders, with emphasis on myopia in human eyes are described herein. The apparatuses used to practice this method alter the defocus equilibrium of the eye to influence dimensional eye growth in a direction towards emmetropia. In particular, myopic defocus is induced in the eye to retard the progression of myopia. It is important that myopic defocus is introduced when normal visual tasks can be maintained throughout the treatment. This means that a focused image can be maintained at the central retina during the treatment. A transparent layer or a reflective layer in the form of a visual display unit provides a platform for projecting various kinds of primary visual content that in turn will form a focused image on the retina. At the same time, the transparency or reflectance of the layer allows secondary objects to be seen. Areas on the layer which do not provide the primary visual content may provide the transparency or the reflectance. Alternatively, the objects, including text or graphics themselves may also be partially transparent or reflective so that any other objects directly behind the transparent objects, or in front of the reflective objects, can be seen by the viewer as overlapped defocused images. Regardless how the transparency or reflectance is provided the primary visual content on the layer (e.g. text, graphic) plays dual critical roles as the object of interest and the necessary visual clues for the viewer to lock his ocular accommodation and focus on the plane of the transparent or reflective layer. The transparent or reflective layer alone will not act as an effective target for the viewer to lock his accommodation and will not achieve the desired function unless visual content is displayed on them. According to optics principle, objects seen behind the transparent layer or in front of the reflective layer will be projected in front of the retina. Therefore, it is an effective means for simultaneously providing clear viewing and myopic defocus. Furthermore, an advantage of the system and method herein is that it does not involve the use of specialty lenses and therefore can be widely applied to children and young adults.

Figure 1B:
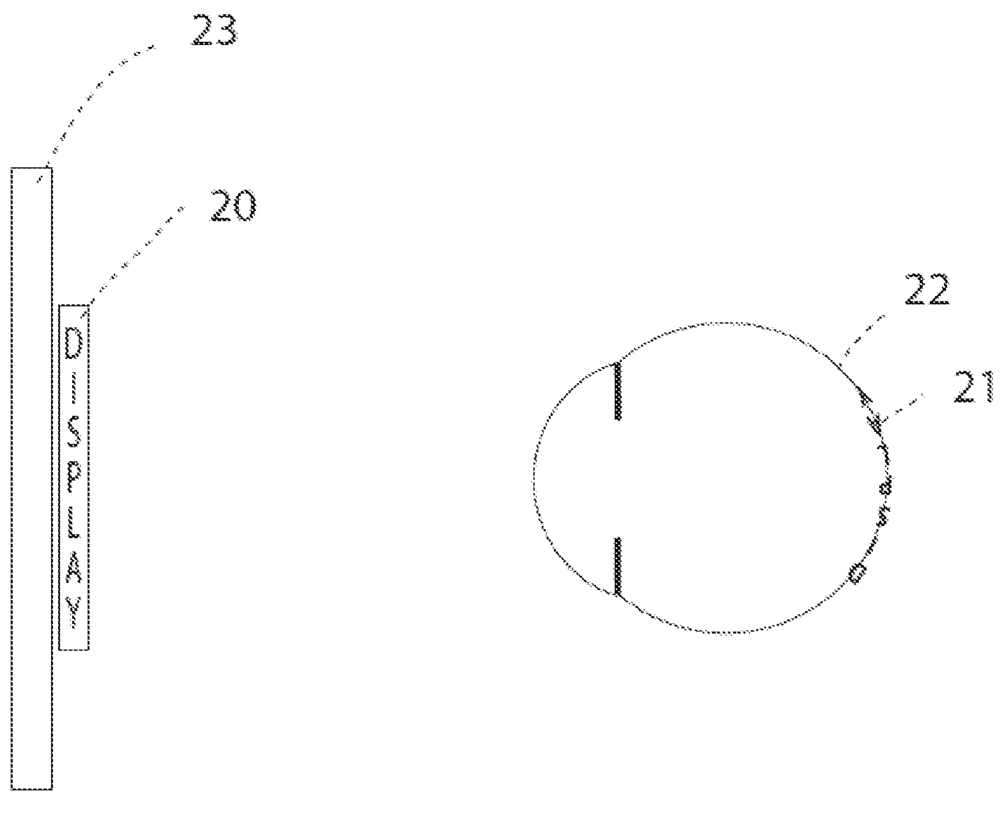
FIG. 1B is a schematic optical diagram of an eye viewing the conventional visual display unit of FIG. 1A.

FIG. 1A shows the way a conventional visual display unit is usually installed and used for viewing. The conventional visual display unit 11 does not include transparent or reflective region in contrast to, for example, FIG. 2A at 31 or FIG. 4A at 81. Also, it may be positioned near an object 12, which is shown as a background object in the figure, which may lack significant visual details. As shown in FIG. 1B, a conventional visual display unit 20, when being viewed, produces focused image 21 on the retina 22. The object 23 behind the unit is occluded and does not provide any image on the central retina. Although the object 23 may extend toward periphery beyond the unit 20, it typically will not produce effective myopic defocus because it is located too close to the unit 20 and/or lacks significant visual details.

Figure 2A:
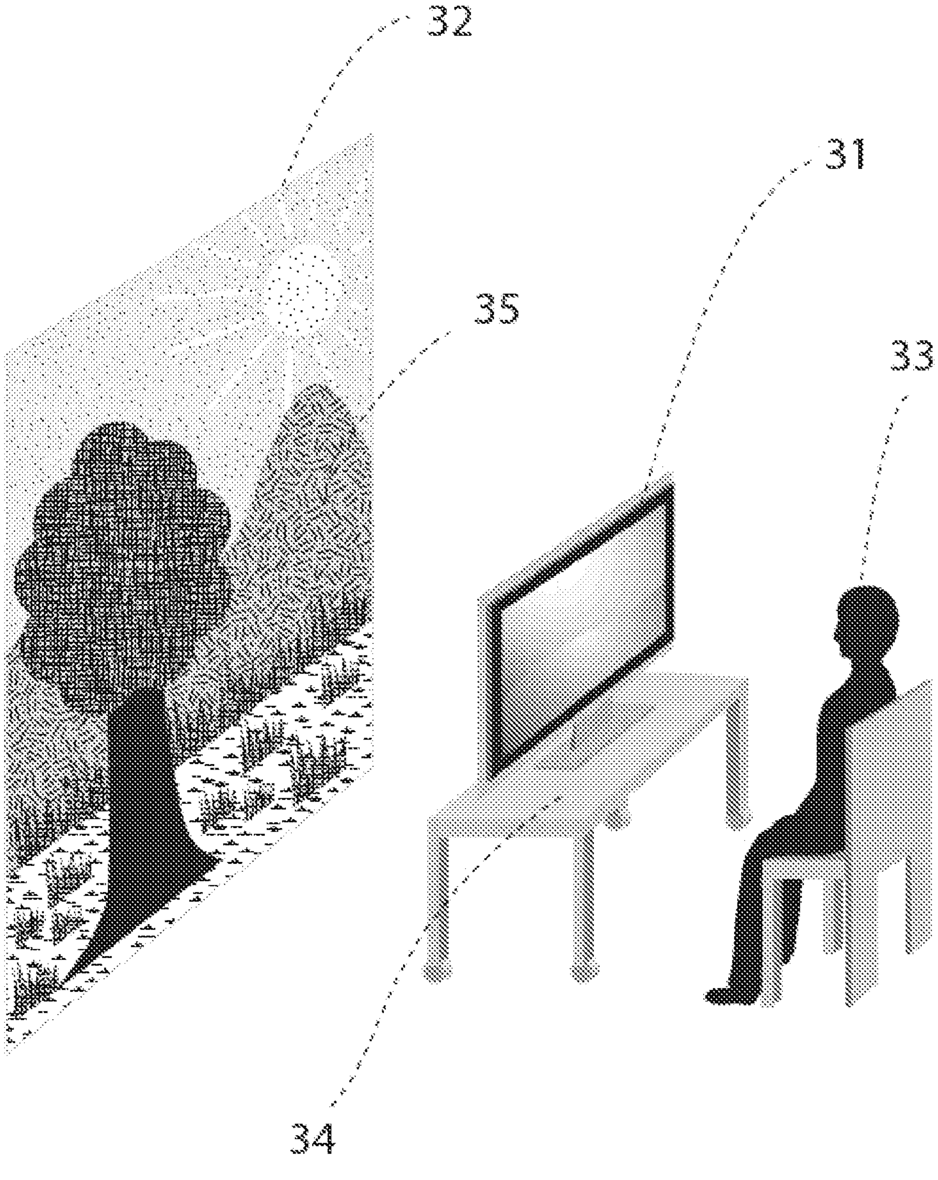
FIG. 2A is a diagram showing an optical system with a transparent layer in accordance with a first embodiment of the present invention.

In a first embodiment of the present invention, a method is provided to introduce a secondary, defocused image in front of the retina while at the same time introducing a focused image on the retina as a primary image which continuously receives attention from the viewer by means of a transparent layer. With reference to FIG. 2A, this is specifically achieved by providing an object, such as a back layer 32, in front of the viewer 33, a transparent layer 31 between the viewer 33 and the back layer 32, and subsequently a primary image on the transparent layer for the viewer's attention. The object can be either a physical object and/or an image of an object. Preferably it is some form of text or graphic on which the viewer actively adjust his/her ocular accommodation and focus. The transparent layer 31 can be in the form of a visual display unit, such as a transparent television screen, as shown in the figure. The transparency of the transparent layer 31 allows the back layer 32 behind to be viewed as a secondary image, which is projected in front of the central region of the retina to generate myopic defocus. The object may also extend towards the periphery so that the secondary image may also project a defocused image on the peripheral retina to further boost the treatment effect. As used herein, "in front of the central region of the retina" means that the secondary image is focused on a plane at least 0.25 diopter away from the retina to the vitreous side. Preferably, the dioptric distance is from about 2 to about 3 diopters. One skilled in the art understands that this measurement of diopters is standard in the field of ophthalmology and need not be discussed in detail here. In an embodiment herein the transparency of the transparent layer is adjustable, or adjustable from about 70% to about 100% transparency, to control the amount of the secondary image to be viewed. As shown in FIG. 2A, the transparent layer 31 is positioned between the back layer 32 and the viewer 33 with the aid of some supporting structure 34. In an embodiment herein the optional supporting structure 34 is connected to the transparent layer 31 so as to physically hold it in place and to prevent it from moving significantly with respect to the back layer. Many different types of supporting structures such as a rack, a stand, a wire, an arm, and a combination thereof, may be used herein, either alone or in conjunction with each other. As used herein a supporting structure may also include a structure which suspends the transparent layer from, for example a ceiling.

In the method and methods herein, the goal is to stop progression and/or cure the eye refractive disorder by encouraging the viewer's eye to either stop growing in a certain direction, to encourage the viewer's eye to grow in another direction, and/or to grow to a certain, more optimal, shape. Thus, to increase effectiveness, the methods herein may require repeated, continuous use by the viewer for an extended period of, for example, more than 1 week; or from about 1 week to 15 years; or from about 1 month to about 10 years; or from about 2 months to about 7 years. In an embodiment herein the method herein includes the repeated viewing of the system herein over a period from about 3 months to about 5 years.

In an embodiment herein the object for producing the secondary image is a fixed or changeable wallpaper showing a landscape such as a forest or a mountain or a picture such as shown in FIG. 2A. It is preferred that such a picture contains visual content of sufficient contrast and a range of spatial frequencies, which are shown to be pre-requisites for the myopic defocus to be corrected detected by the eye. (Tse, Chan et al. 2004; Diether and Wildsoet 2005) Specifically, it is preferred that the picture contains visual content with contrast of more than 10%, or preferably from about 25% to about 75%, as measured by image capture using video camera followed by quantification of pixel brightness level. It is also preferred that the picture contains spatial frequencies ranged from 0.02-50 cycle/deg measured by image capture using video camera, followed by spatial frequency analysis using discrete fourier transformation. The preferred optical distance between the layer on which the primary image is provided and the object to provide the secondary image is from about 0.25 to about 6 diopters, or from about 0.5 to about 4 diopters, or from about 2 to about 3 diopters. The optical distance can be measured by quantifying the power of the lens needed to neutralize the defocus, or by measuring the physical dimensions of all optical components, and followed by optical ray tracing.

In an embodiment herein the level of myopic or hyperopic defocus is specifically customized to counter the level of myopia or hyperopia of the viewer, especially, where, for example, the system is provided on, in and/or incorporating an electronic device such as a tablet computer, personal computer, smart phone, etc. that is typically used by a single person.

Figure 2B:
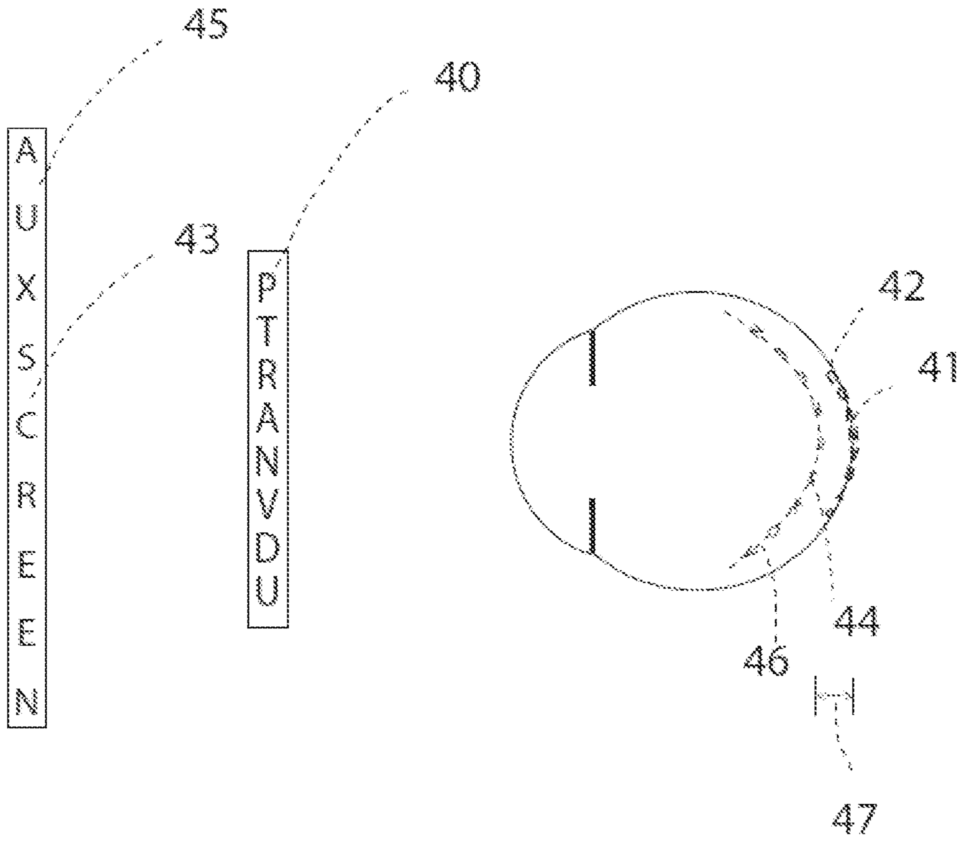
FIG. 2B is a schematic optical diagram of an eye viewing the transparent layer of the optical system of FIG. 2A showing the generated myopic defocus.

Referring to FIG. 2B, the viewer typically intentionally brings the primary image displayed by the transparent layer 40 into focus using ocular accommodation. Depending on the existing refractive error of the viewer, conventional spectacle correction may be needed (not shown in the figure) for the viewer to focus the primary image on the retina. The primary image displayed on the front layer 40 is projected in the eye as focused image 41 on the central portion of the retina 42. Simultaneously, the secondary visual content 43 of the back layer is projected in the eye as a myopically defocused secondary image 44 in front of the central region of the retina 42. The defocused secondary image 44 in front of the central retina serve as a major source of myopic defocus 47 signal for retarding myopia progression. The back layer may optionally further extend towards the periphery 45 so as to project additional myopically defocused image 46 on regions of the retina other than the central region.

The embodied optical system can be modified further, for example, it may contain a visual display unit having more than one transparent layer. The primary visual contents may be displayed on a front transparent layer as the primary image for continuous viewing by the user. Secondary visual contents which form the secondary image as the visual cues of myopic defocus, not requiring the user's attention, may be displayed on at least one back layer for constructing the defocused images.

Figure 3A:
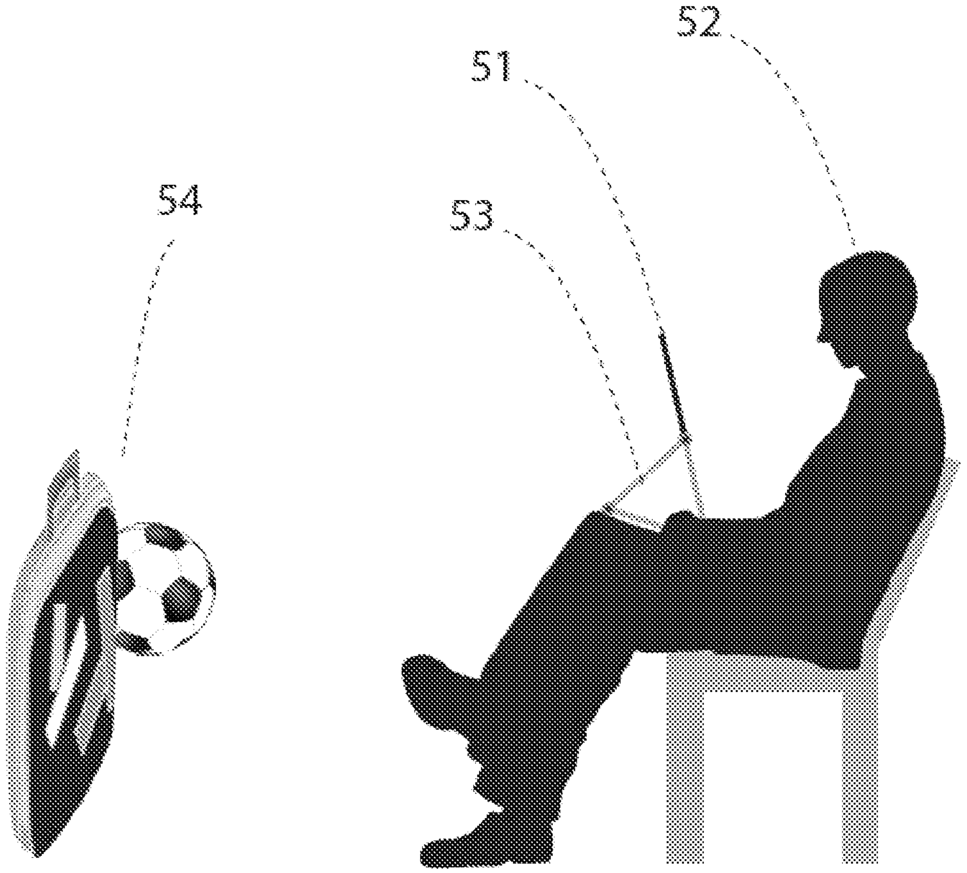
FIG. 3A is a diagram showing a portable system with the optical system of FIG. 2A.

FIG. 3A shows a simplified optical system with a single transparent layer as a visual display. The system is embodied as a compact form of a portable electronic device such as an electronic book reader unit 51. In an embodiment herein the portable electronic device herein may include an electronic book reader, a mobile phone, an electronic tablet, a computer, a personal digital assistant, a watch, a headwear, an eyewear, a wireless display, a holographic projector, a holographic screen, an augmented reality device, and a combination thereof. A transparent layer which functions as a display screen is positioned and controlled in an upright position close to the viewer 52 by means of mechanical supporting structures such as a rack 53, which becomes portable when folded. The supporting structure(s) can be connected either permanently or temporarily to the transparent layer. Random objects 54 may present in the background environment behind the unit 51. Depending on the existing refractive error of the viewer, conventional spectacle correction may be needed (not shown in the figure) for the viewer to focus the primary image on the retina.

Figure 3B:
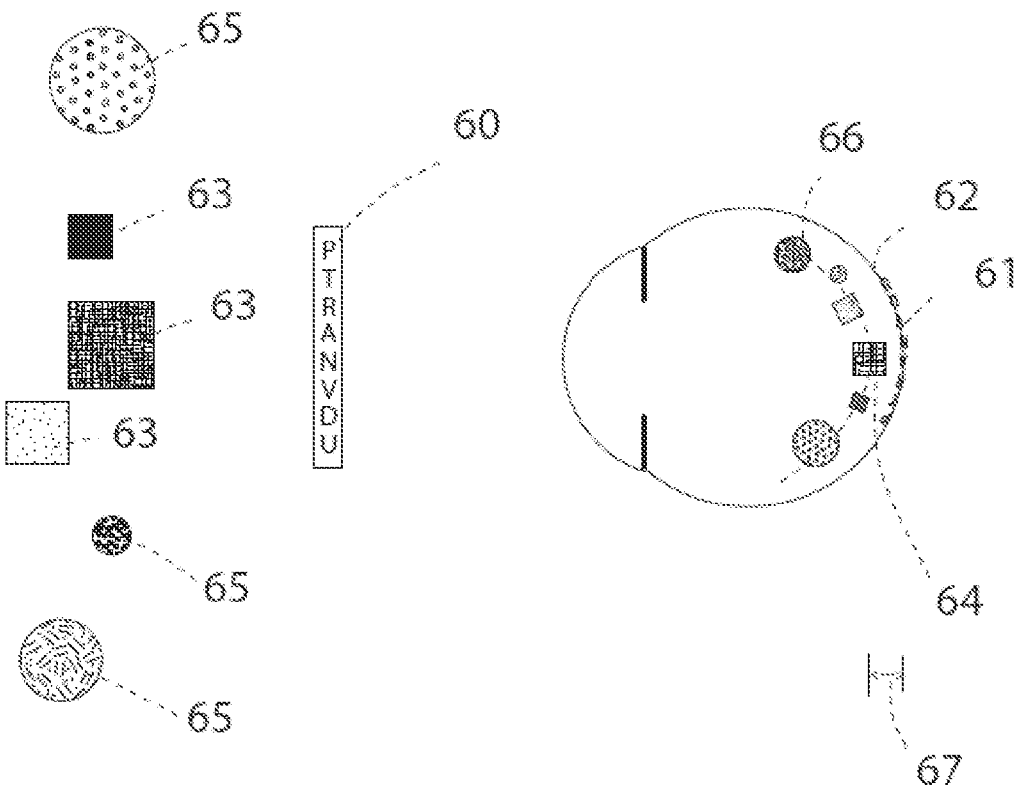
FIG. 3B is a schematic optical diagram of an eye viewing the portable system of FIG. 3A showing the generated myopic defocus.

Referring to FIG. 3B, the viewer exerts ocular accommodation to bring the primary image as displayed by the transparent layer to focus. As a result, visual content such as text and graphics as shown on the transparent layer 60 are projected on the retina 62 as a focused primary image 61. As the user carries and uses the unit in different visual environments, random visual objects 63 and 65 enter the visual field of the viewer. Objects 63 behind the transparent layer 60 are visible to the viewer as secondary images 66 and are projected to form myopically defocused images in front of the central retina 64. Those defocused secondary images serve as major source of myopic defocus 67 signal for retarding myopia progression. Other objects 65 in the peripheral visual field that are positioned more distant from the unit can also project myopically defocused secondary images 66 on other parts of retina. Those images also serve as auxiliary sources of myopic defocus 67 for retarding myopia progression. Preferably, the transparency of the transparent layer is adjustable, either manually and/or automatically, to control the amount of background objects to be viewed.

Alternatively, in an embodiment herein, the optical system, for example, the unit 51 of FIG. 3A, can be an electronic device which generates both the primary and the secondary images on the same or different layers, for example, to provide a focused primary image and a defocused secondary image simultaneously on the same display screen.

Preferably, the transparency of the display screen of the unit 51 is adjustable and more preferably controllable, for example, by electronic means such as transparent organic light emitting diode, in order to maintain and optimize the legibility of the visual content under different environments and according to personal preference.

In another embodiment of the present invention, it is provided a method to introduce myopic defocus by providing a layer having a reflective surface facing the viewer, at least one object facing the reflective surface, and subsequently a primary image with visual contents as text and graphics on the layer, with the primary image being viewable by the viewer. Again the object can be either a physical object and/or an image of an object. The reflective surface allows the reflection of the object to be viewed by the viewer as a secondary image, and the secondary image is focused in front of the central region of the retina of the viewer. The objects can be positioned behind the viewer and/or in between the viewer and the reflective surface.

Figure 4A:
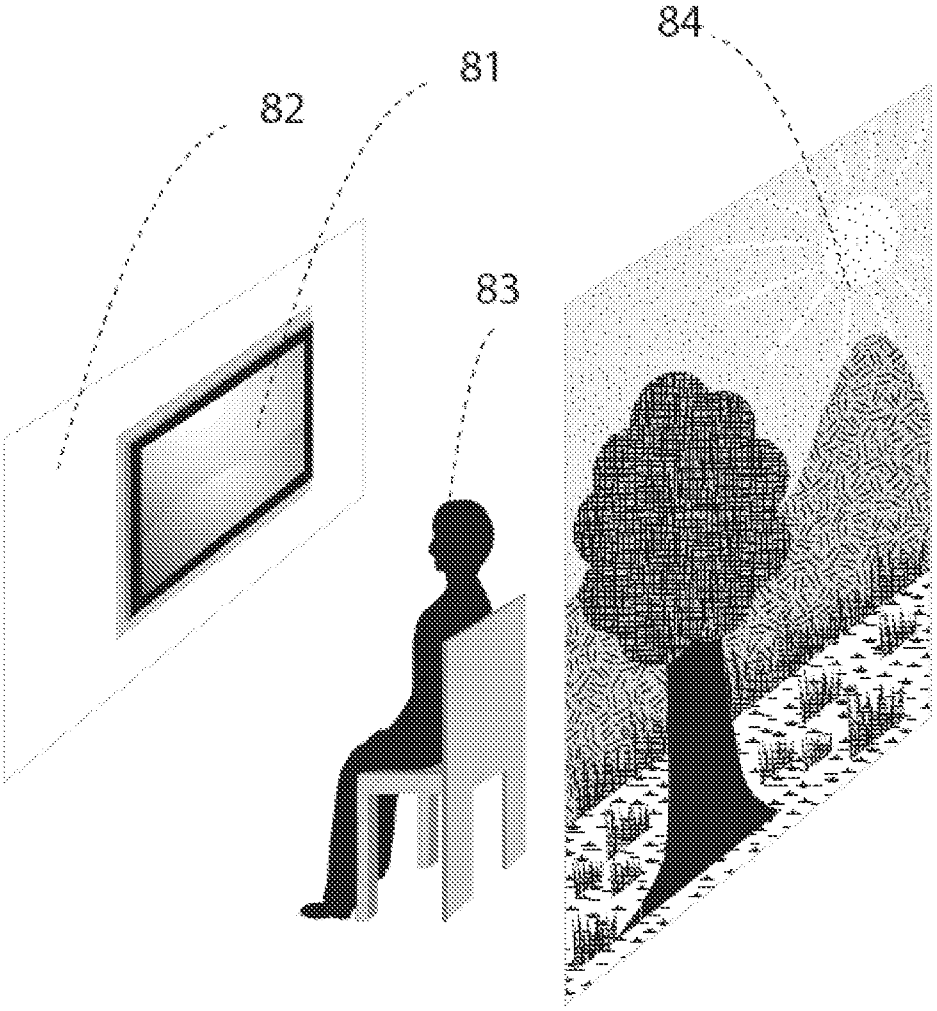
FIG. 4A is a diagram showing the way an optical system with a reflective layer in accordance with a second embodiment of the present invention.

In an embodiment herein, the reflective layer may be a visual display unit adapted to provide a primary image of a principal visual content. With reference to FIG. 4A, a method herein comprises the step of providing an object 84, such as a back layer, behind a viewer 83, and further providing a layer 81 having a reflective surface 82, such as a mirror or a display screen with reflective surface, facing the viewer 83 and the object 84. A primary image is then provided on the layer 81 for the viewer's attention. The reflectance of the reflective surface 82 allows the back layer behind the viewer to be viewed by the viewer as a reflection, and the reflection is projected in front of the retina to generate myopic defocus. The object for producing the secondary image can be fixed or changeable wallpapers behind the viewer showing landscapes such as a forest or a mountain or any pictures. It is preferred that the secondary image contains a detailed pattern having sufficient contrast and a range of spatial frequency, which is a prerequisite for the projected myopically defocused image be detected by the retina. For example, a projected landscape photo or wallpaper 84 is used in the system in FIG. 4A.

Figure 4B:
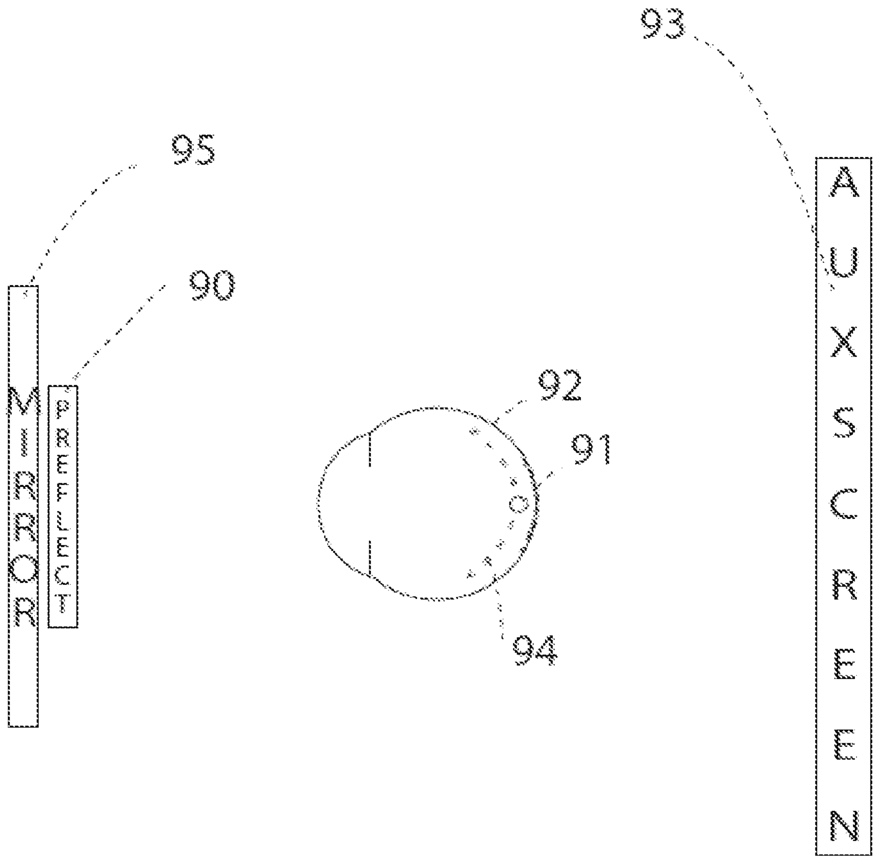
FIG. 4B is a schematic optical diagram of an eye viewing the optical system of FIG. 4A showing the generated myopic defocus.

With reference to FIG. 4B, the viewer intentionally brings the primary image displayed by the layer 90 into focus using ocular accommodation. Depending on the existing refractive error of the viewer, conventional spectacle correction may be needed (not shown in the figure) for the viewer to correctly focus the primary image on the retina. The primary image displayed on the front layer 90 is projected in the eye as focused image 91 on the central region of the retina 92. Simultaneously, the object 93 behind the viewer providing the visual content reflected by the mirror 95 and is projected in the eye as a myopically defocused secondary image 94 in front of the central region of the retina 92. The defocused secondary image 94 in front of the central retina serve as a major source of myopic defocus signal for retarding myopia progression. The object 93 may optionally further extend towards the periphery so as to project additional myopically defocused image on the peripheral retina to further boost the treatment effect.

Preferably, the light reflectance of the reflective surface is adjustable so as to control the clarity or legibility of the primary object to be viewed. As shown in FIG. 4A, the layer 81 is facing the viewer 83 and the back layer 84 by mounting onto the wall. Alternatively, the layer 81 can be connected to or supported by a supporting structure. Many different supporting structures such as a rack, a stand, a wire, an arm, and a combination thereof, may be used herein, either alone or in conjunction with each other. As used herein a supporting structure may also include a structure which suspends the layer.

The optical system as embodied above can be further modified. For example, it may contain a visual display unit having more than one layer. The primary visual contents are displayed on a front layer as the primary image for viewing continuously by the user. Secondary visual contents which form the secondary image as the visual cues of myopic defocus, not requiring the user's attention, are displayed on at least one back layer for constructing defocus images.

Figure 5A:
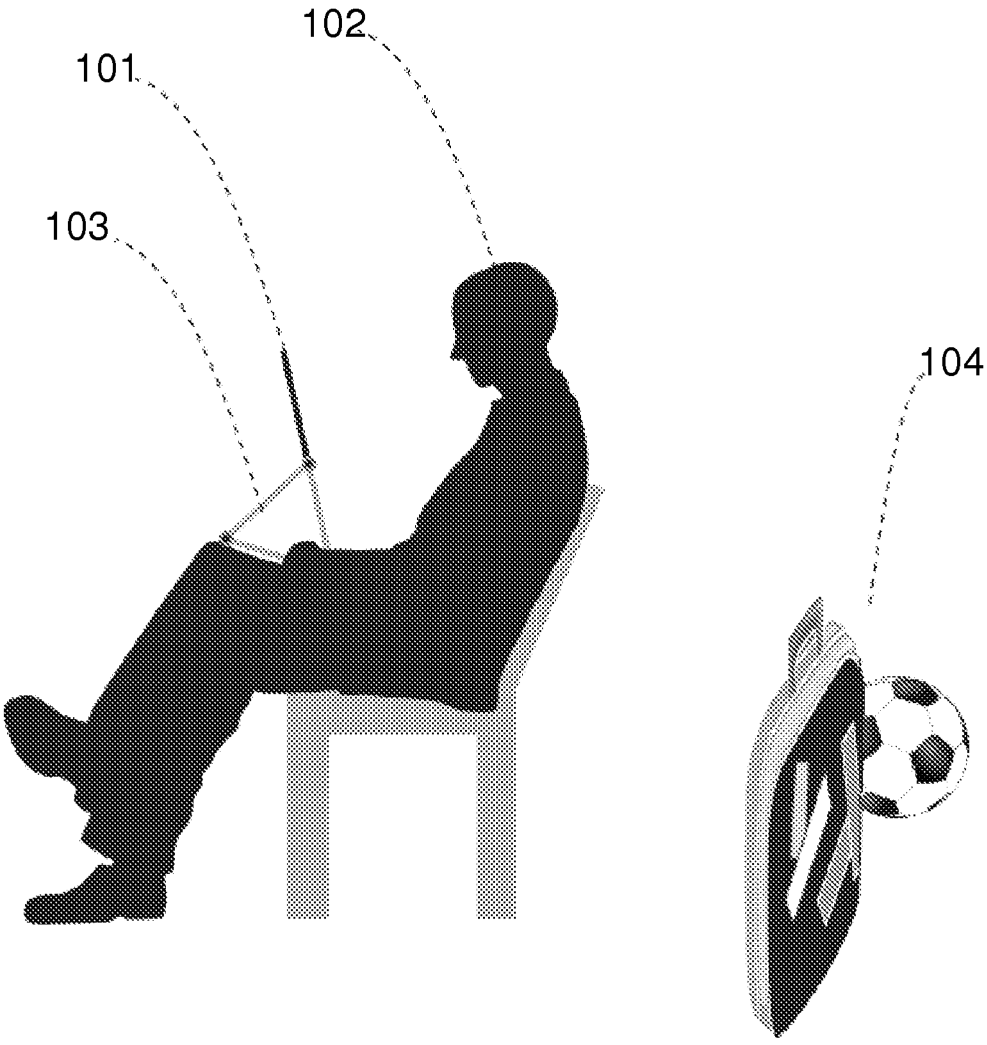
FIG. 5A is a diagram showing a portable system with the optical system of FIG. 4A.

FIG. 5A shows a simplified optical system with a single reflective layer as a visual display. The system is embodied as a compact form of a portable electronic device such as an electronic book reader unit 101. The layer which functions as a display screen is connected to and is positioned in an upright position close to the viewer 102 by means of mechanical supporting structures such as a rack 103, which may become portable when folded. Random objects 104 may present anywhere in front of the unit 101. Depending on the existing refractive error of the viewer, conventional spectacle correction may be needed (not shown in the figure) for the viewer to focus the primary image on the retina.

Figure 5B:
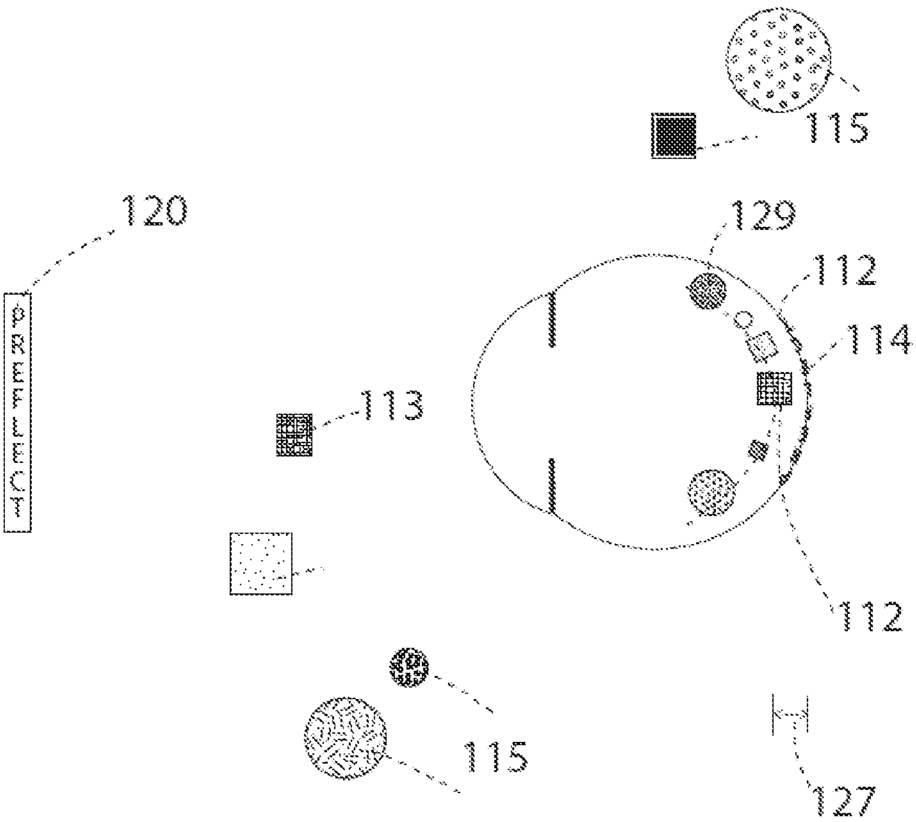
FIG. 5B is a schematic optical diagram of an eye viewing the portable system of FIG. 5A showing the generated myopic defocus.

Referring to FIG. 5B, the viewer exerts ocular accommodation to bring the primary image as displayed by the layer to focus. As a result, visual content such as text and graphics as shown on the unit are projected on the retina 112 as a focused primary image 114. As the user carries and uses the unit in different visual environments, random secondary visual objects 113 and 115 enter the visual field of the viewer. Objects 113 facing the reflective surface of the layer 120 are visible to the viewer as secondary images 122 and are projected to form myopically defocused images in front of the central retina. Those defocused secondary images serve as major source of myopic defocus 127 signal for retarding myopia progression. Other objects 115 in the peripheral visual field that are positioned more distant from the unit can also project myopically defocused secondary images 129 on other parts of retina. Those images serve as auxiliary sources of myopic defocus 127 for retarding myopia progression.

Preferably, the light reflectance of the reflective surface of the unit 101 is adjustable and more preferably controllable, for example, by electronic means such as the top emitting OLED technology, in order to maintain and optimize the legibility of the visual content under different environments and personal preference.

Figure 6:
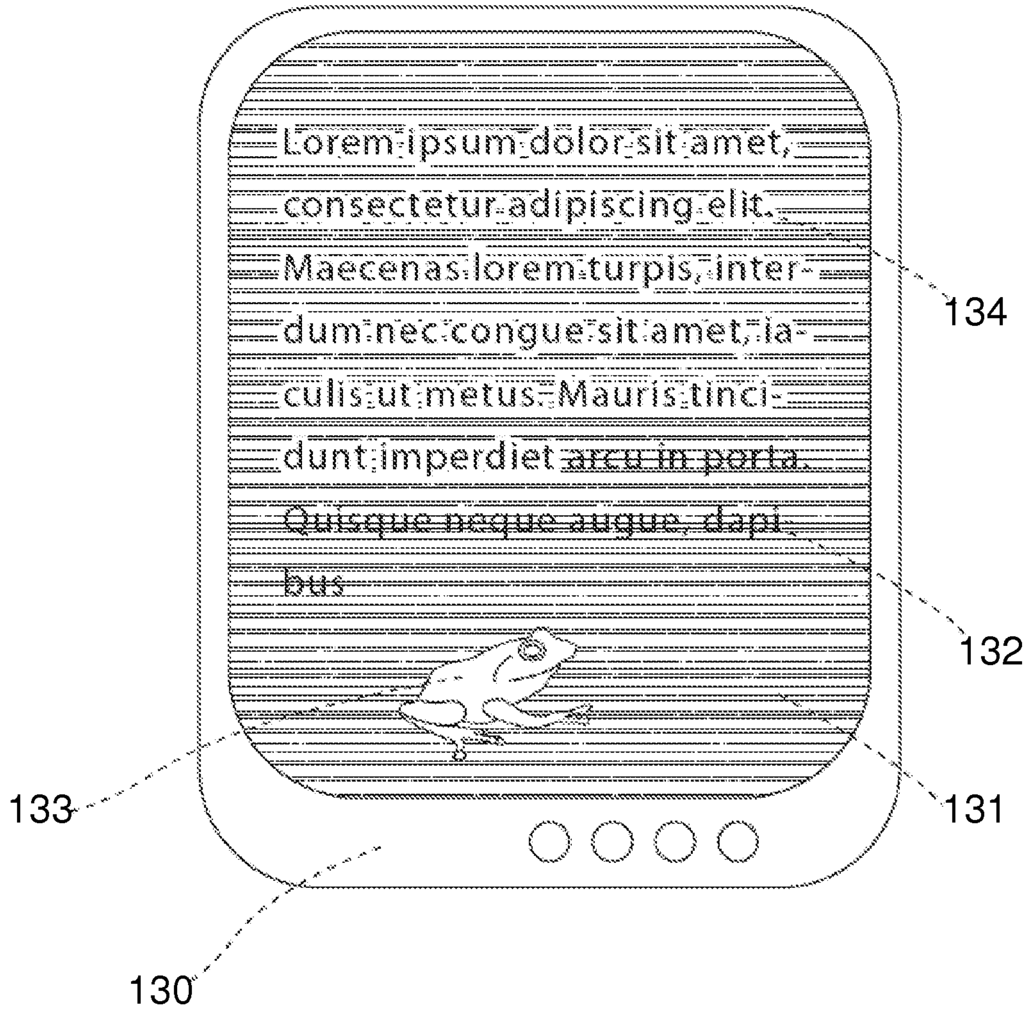
FIG. 6 is a diagram of a portable visual display unit employing a transparent layer or a reflective layer, and a contrast enhancing technology in accordance with an embodiment of the present invention. The shade represents the transparent layer or the reflective layer.

FIG. 6 describes an example of electronic book reader unit 130 employing a transparent or reflective displaying layer as embodied in the present invention. The unit 130 uses a contrast enhancement technology to prevent the displayed text or graphic from losing legibility due to the confusion from the defocused images of the objects behind the layer. For example, in one embodiment, an organic light emitting diode display can be used to display the primary image. Idle area 131 of the layer without text 132 or graphic 133 remains transparent or reflective (as depicted by the line-shaded areas in the figure). The displayed texts or graphics are deliberately surrounded by edges 134 of a contrasting color relative to the color of the texts or graphics to enhance contrast. For example, white text may be surrounded by black edge, or blue text may be surrounded by yellow edge, etc. In an embodiment herein the primary image (herein including text), contains at least one edge, and the edge is surrounded by a contrasting color.

The capability of the current invention to treat myopia and hyperopia is supported by the applicants' previous study using an animal model (Tse and To 2011), which showed that myopic defocus and hyperopic defocus may be introduced to the eye using a dual-layer viewing system. In that study, the front layer of the dual-layer system was made to become partially transparent so that the back layer can be seen. When properly controlled, the back layer may produce myopic defocus while the front layer may produce hyperopic defocus. It was shown that the refractive error of the eye was modulated by the amount of myopic defocus, hyperopic defocus or (more precisely) that the ratio between them produced by the dual-layer system in a controllable manner. Therefore, it appears feasible that similar multi-layer viewing systems may be applied to treat human refractive error through the use of a transparent layer or its variant as reflective layer.

Figure 7:
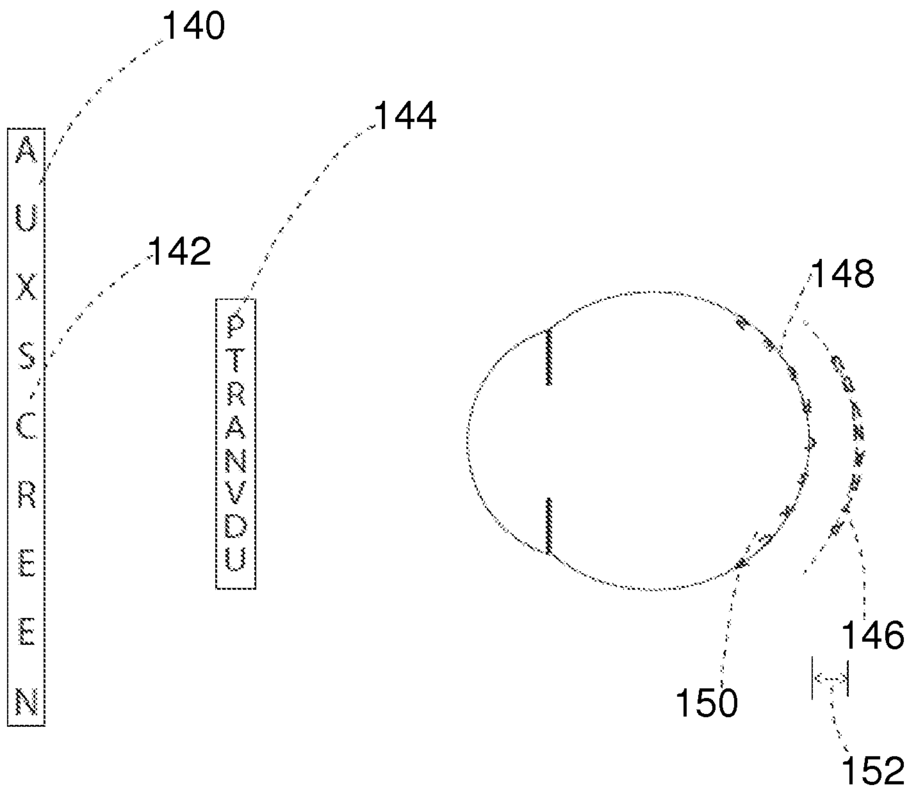
FIG. 7 is a schematic optical diagram of an eye viewing the optical system of FIG. 2A showing the generated hyperopic defocus.

FIG. 7 shows a further embodiment of the present invention which relates to an optical system for treating hyperopia. Primary visual contents 142 are displayed by the back layer 140 for viewing, while secondary visual contents which do not require attention from the viewer are displayed by the front transparent layer 144. When the user consciously focuses on the back layer 140 using ocular accommodation, the image of the primary visual contents displayed on the back layer 140 are projected in the eye as focused primary image 148. Secondary visual content on the front transparent layer 144 are projected in the eye behind the retina 150 as hyperopically defocused secondary image(s) 146. The defocused image serves as a major source of hyperopic defocus 152 stimuli for accelerating eye growth and reducing hyperopia.

The examples herein are for the facilitation of understanding and are not to be construed as limiting in any way upon the scope of the invention. It is expected that one skilled in the art will be able to envision other embodiments of the invention based on a full and complete reading of the specification and the appended claims. All relevant parts of all references cited or described herein are incorporated by reference herein. The incorporation of any reference is not in any way to be construed as an admission that the reference is available as prior art with respect to the present invention.

REFERENCES

Diether, S. and C. F. Wildsoet (2005). "Stimulus requirements for the decoding of myopic and hyperopic defocus under single and competing defocus conditions in the chicken." *Invest Ophthalmol Vis Sci* 46(7): 2242-2252.

Tse, D. Y. and C. H. To (2011). "Graded competing regional myopic and hyperopic defocus produce summated emmetropization set points in chick." *Investigative ophthalmology & visual science* 52(11): 8056-8062.

Tse, Y., J. Chan, et al. (2004). *Spatial frequency and myopic defocus detection in chick eye in a closed visual environment*. ARVO, Fort Lauderdale.

We claim:

1. A method for retarding or reversing progression of myopia a viewer, the viewer having a retina with a central region, the method comprising the steps of:

providing a layer having a reflective surface, said reflective surface facing the viewer;

providing an object facing the reflective surface; providing a primary image on the layer, said primary image being viewable by the viewer; wherein the reflective surface allows reflection of the object to be viewed by the viewer as a secondary image, with the secondary image being focused in front of the central region of the retina; wherein the secondary image generates myopic defocus.

2. The method according to claim 1, wherein the primary image is focused on the retina.

3. The method according to claim 1, wherein the reflective surface has an adjustable reflectance.

4. The method according to claim 1, wherein the primary image is focused on the retina by ocular accommodation of the viewer or by using optical lens.

5. The method according to claim 1, comprising a contrast enhancement technology.

* * * * *